US011904188B2

(12) United States Patent
Fu et al.

(10) Patent No.: US 11,904,188 B2
(45) Date of Patent: Feb. 20, 2024

(54) FULLY-SPHERICAL RADIATION THERAPY SYSTEM

(71) Applicant: BEIJING RAYER SHIWEI MEDICAL RESEARCH CO., LTD, Beijing (CN)

(72) Inventors: Dongshan Fu, Beijing (CN); Zhenyu Gu, Beijing (CN); Yabo Wang, Beijing (CN); Lujun An, Beijing (CN)

(73) Assignee: BEIJING RAYER SHIWEI MEDICAL RESEARCH CO., LTD, Beijing (CN)

(*) Notice: Subject to any disclaimer, the term of this patent is extended or adjusted under 35 U.S.C. 154(b) by 0 days.

(21) Appl. No.: 18/036,276

(22) PCT Filed: Jul. 26, 2022

(86) PCT No.: PCT/CN2022/107804
§ 371 (c)(1),
(2) Date: May 10, 2023

(87) PCT Pub. No.: WO2023/005902
PCT Pub. Date: Feb. 2, 2023

(65) Prior Publication Data
US 2023/0390589 A1    Dec. 7, 2023

(30) Foreign Application Priority Data

Jul. 30, 2021  (CN) .......................... 202110871185.3

(51) Int. Cl.
*A61N 5/10*    (2006.01)
(52) U.S. Cl.
CPC ......... *A61N 5/1084* (2013.01); *A61N 5/1049* (2013.01); *A61N 5/1083* (2013.01)

(58) Field of Classification Search
None
See application file for complete search history.

(56) References Cited

U.S. PATENT DOCUMENTS

| 2004/0184579 A1 | 9/2004 | Mihara et al. |
| 2007/0071176 A1 | 3/2007 | Main et al. |

(Continued)

FOREIGN PATENT DOCUMENTS

| CN | 101015723 A | 8/2007 |
| CN | 101209368 A | 7/2008 |

(Continued)

OTHER PUBLICATIONS

International Search Report and Written Opinion of the International Searching Authority issued for International PCT Application No. PCT/CN2022/107804 dated Oct. 14, 2022.

(Continued)

*Primary Examiner* — Hoon K Song
(74) *Attorney, Agent, or Firm* — Howson & Howson LLP

(57) ABSTRACT

Provided is a fully-spherical radiation therapy system. The fully-spherical radiation therapy system includes a multi-degree-of-freedom robot, a linear accelerator and a double-image-guided positioning mechanism. The double-image-guided positioning mechanism includes four ray sources and two ray detectors, and the four ray sources include a first ray source, a second ray source, a third ray source and a fourth ray source. An intersection of two beams emitted by the first ray source and the second ray source is a low-level treatment center, an intersection of two beams emitted by the third ray source and the fourth ray source is a high-level treatment center, and the low-level treatment center and the high-level treatment center form a fully-spherical treatment space for multiple treatment nodes of a spherical center.

4 Claims, 15 Drawing Sheets

(56) References Cited

U.S. PATENT DOCUMENTS

| | | | |
|---|---|---|---|
| 2012/0106704 A1* | 5/2012 | Maurer, Jr. | G16H 20/30 |
| | | | 378/65 |
| 2017/0239496 A1 | 8/2017 | Sun et al. | |
| 2019/0038918 A1* | 2/2019 | Lu | A61N 5/1039 |
| 2020/0175733 A1* | 6/2020 | Yu | A61B 6/5282 |
| 2020/0406064 A1 | 12/2020 | Maltz et al. | |
| 2022/0000436 A1* | 1/2022 | Jacobson | A61N 5/1071 |
| 2022/0370833 A1 | 11/2022 | Yonemoto et al. | |
| 2023/0017353 A1* | 1/2023 | Bai | A61B 6/4452 |

FOREIGN PATENT DOCUMENTS

| | | |
|---|---|---|
| CN | 103143124 A | 6/2013 |
| CN | 104548375 A | 4/2015 |
| CN | 104587609 A | 5/2015 |
| CN | 105031833 A | 11/2015 |
| CN | 107362464 A | 11/2017 |
| CN | 108744310 A | 11/2018 |
| CN | 110812717 A | 2/2020 |
| CN | 212235656 U | 12/2020 |
| CN | 112972912 A | 6/2021 |
| CN | 113491844 A | 10/2021 |

OTHER PUBLICATIONS

First Office Action issued for Corresponding Chinese Patent Application No. 202110871185.3 dated Jan. 21, 2022.
Second Office Action issued for Corresponding Chinese Patent Application No. 202110871185.3 dated Mar. 15, 2022.

* cited by examiner

FULLY-SPHERICAL RADIATION THERAPY SYSTEM

CROSS-REFERENCE TO RELATED APPLICATIONS

This is a National Stage Application filed under 35 U.S.C. 371 based on International Patent Application No. PCT/CN2022/107804, filed on Jul. 26, 2022, which claims priority to Chinese Patent Application 202110871185.3 filed on Jul. 30, 2021, disclosures of both of which are incorporated herein by reference in their entireties.

TECHNICAL FIELD

The present application relates to radiosurgery robotic systems, for example, a fully-spherical radiation therapy system.

BACKGROUND

Image guided radiation therapy (IGRT) refers to a new technology of tumor radiotherapy which is gradually developed in a recent dozen of years. Through advanced image equipment and image processing methods, in a treatment planning stage, precise target volume detection and delineation, treatment beam distribution planning and dose distribution calculation are performed for a patient. Precise target volume positioning is performed before the treatment radiation and target volume motion tracking is performed during the treatment so that the precise radiotherapy of a tumor is achieved and the damage to normal tissues and critical organs around the tumor is reduced.

A radiosurgery robotic system is a piece of special equipment for radiosurgery therapy, and is mainly used for precise radiotherapy of solid tumors of the whole body. CyberKnife, a radiosurgery robotic system developed by a company, Accuray, of the US, can achieve precise image-guided radiation therapy in combination with advanced technologies such as modern robots and miniature linear accelerators. CyberKnife can treat tumors of different sizes through hypofractionated radiation (one time to five times) and has been widely used clinically in the world.

The radiosurgery robotic system based on a multi-degree-of-freedom robot requires an ideal fully-spherical treatment space so that the treatment beam of an accelerator can be projected to a target volume of the patient from different positions and different directions of the sphere, the optimal treatment dose distributions can be achieved, and the best treatment effect is obtained. The treatment center of the radiosurgery system is the reference point for the entire system. The sphere is defined with the treatment center as the center of the sphere, and multiple (up to thousands) nodes evenly distributed on the sphere are planned and are called fully-spherical treatment nodes. The set of all treatment nodes on the sphere is the fully-spherical treatment space. A treatment planning system selects optimized treatment nodes (tens to hundreds) for specific patients from the fully-spherical treatment space to satisfy the clinical requirements for optimal dose distributions.

One of the major drawbacks of the radiosurgery robotic system based on the multi-degree-of-freedom robot is the limited treatment space, which, as shown in FIG. 1, is more than half a sphere rather than an ideal full sphere. The treatment center at a low position is referred to as a low-level treatment center. The treatment is performed at the low-level treatment center; the robot carrying the accelerator can reach most spatial positions above and on two sides of the patient without collision with the treatment couch and the patient, so that a low-level treatment center treatment space of more half a sphere is formed. However, the treatment is usually performed when the patient is in a supine position. For the target volume near the back, such as the target volume of the spine and the target volume of the thorax and the abdomen near the back, the limited treatment space limits the radiation of the treatment beam from the bottom position and positions around the bottom position of the patient, so that the treatment plan cannot achieve the optimal treatment dose distributions satisfying the clinical requirements. In actual clinical applications, the patient may change to a prone position for the treatment of the target volume near the back so that the requirements of treatment dose distributions are satisfied. However, the motion of the target volume near the back caused by breathing will reduce the precision of the treatment, extend the treatment time, and thus make clinical operations during the treatment more complicated.

The related art discloses a non-invasive robotic radiation therapy system, and the technical feature thereof is that a large-size mechanical G-arm and a G-arm guide rail of an image-guided device are mounted. However, due to the large-size and complicated mechanical structure of the G-arm, the sliding precision of an X-ray source is difficult to control; as a result, the X-ray source needs to be recalibrated after sliding in place. No matter whether the G-arm is mounted on the ground or hung from the ceiling, no matter where the treatment center is located, and no matter how many treatment centers are provided, the G-arm will certainly block the treatment space and affect spatial positions which can be reached by the linear accelerator due to the large space occupied by the G-arm, so that the linear accelerator cannot reach the fully-spherical treatment space.

The related art discloses a robotic radiation therapy system, which is composed of six modules, which are, a forward-inverse radiation therapy planning system, a three-dimensional numerical control treatment couch, an automatic real-time image tracking system, a robotic system, a ray source and a real-time dose verification system. The automatic real-time image tracking system is composed of a C-arm real-time image system, an infrared automatic tracking locator and an electromagnetic automatic tracking locator. However, the large space occupied by the C-arm will limit spatial positions that can be reached by the linear accelerator, so that a treatment blind zone will be inevitably produced, resulting in a limited spherical treatment space.

The related art discloses a stereotactic radiosurgery treatment device, which is composed of a radiation device system, a six-dimensional robotic treatment couch 1 and a treatment planning system. The radiation device system is composed of a machine frame 12 and a C-shaped machine arm 5. A rotary shaft 10 is disposed on the machine frame 12, the rotary shaft is connected to a guide rail 9 and controls the rotation of the guide rail 9, and the C-shaped machine arm 5 is mounted on the guide rail 9 and performs an arc-shaped motion along the guide rail 9. A ray source 2 is mounted on one end of the C-shaped machine arm 5, a small machine head 3 is mounted on the bottom end of the ray source 2, and a collimator 4 is mounted on the bottom end of the small machine head 3. A telescopic electronic portal imaging device 7 and a movable shielding protection balancing weight 8 are mounted on the other end of the C-shaped machine arm 5. A target organ positioning detection device 6 is mounted on the side of or below the couch surface of the six-dimensional robotic treatment couch 1. A radiation treatment head may make a 90° (or ±45°) rotary motion around an X axis. The treatment device provides treatment rays at positions of multiple radians, and the formed treatment space is the middle part of a sphere.

The related art discloses a radiation therapy setup positioning device and a static and dynamic target volume setup method. A treatment robot has an operating arm, a compact linear electron accelerator is mounted on the end portion of the operating arm of the treatment robot, and a secondary collimator is mounted on the end portion of the compact linear electron accelerator. A robotic treatment couch is disposed at a corresponding position of a double-image C-arm system, a C-arm slide rail laser locator is disposed on the inner side of the double-image C-arm system, a C-arm mounting space left-side locator is disposed at a corresponding position on the outer side of the double-image C-arm system, and two sets of X-ray image systems are provided to achieve binocular imaging. When the C-arm slide rail rotates and only one set of X-ray imaging system is started for use, cone beam computed tomography (CBCT) imaging can be achieved. Similar to the preceding patents, the design of the above patent also has the same problem. That is, this treatment device does not provide a treatment space below the patient.

The related art discloses a circumferential sphere stereotactic radiation therapy device including an X-band accelerator, a multileaf collimator, a treatment couch, an image system, an electronic portal imaging device (EPID), a fixed machine frame and a rotary machine frame. The rotary machine frame is rotatably disposed on the fixed machine frame, the treatment couch is fixed relative to the fixed machine frame, the image system is disposed on the rotary machine frame, the X-band accelerator is connected to the multileaf collimator, and the X-band accelerator is disposed on the rotary machine frame so that the X-band accelerator forms spherical radiation on a treatment center; the EPID is disposed on the rotary machine frame and is orthogonal to beams of the X-band accelerator so as to receive remaining beams. The treatment device provides treatment rays at positions of multiple radians, and the formed treatment space is the middle part of a sphere.

The related art discloses a radiation treatment apparatus includes a guide and a support member. The guide moves a radiation generating unit along an orbit with a predetermined radius such that an X-ray emitted from the radiation generating unit may cross an isocenter. The support member rotates the guide about a turning axis passing through the isocenter. The radiation generating unit is moved along a spherical plane by the guide and the support member and applies the X-ray toward the isocenter in multiple directions. The treatment space formed by the treatment apparatus is the middle part of the sphere.

The related art discloses a method and apparatus for quality assurance of an image guided radiation treatment delivery system. A quality assurance (QA) marker is positioned at a preset position under guidance of an imaging guidance system of a radiation treatment delivery system. A radiation beam is emitted from a radiation source of the radiation treatment delivery system at the QA marker. An exposure image of the QA marker due to the radiation beam is generated. The exposure image is then analyzed to determine whether the radiation treatment delivery system is aligned. However, the accelerator of the above patent has limited moving positions and cannot move to the position below the patient, so that the design of the treatment plan is limited; only a hemispherical treatment space can be obtained, which is not conducive to the treatment of the patient.

SUMMARY

Through the present application, the limitation of the treatment space of the radiosurgery robotic system in the related art can be avoided. The present application provides a fully-spherical radiation therapy system for achieving radiosurgery treatment on a fully-spherical treatment space through two double-image-guided treatment spaces composed of a low-level treatment center and a high-level treatment center, respectively.

The present application provides the technical solution described below.

A fully-spherical radiation therapy system is provided. The fully-spherical radiation therapy system includes a multi-degree-of-freedom robot, a linear accelerator and a double-image-guided positioning mechanism. The double-image-guided positioning mechanism includes four ray sources and two ray detectors, and the four ray sources include a first ray source, a second ray source, a third ray source and a fourth ray source. An intersection of two beams emitted by the first ray source and the second ray source is a low-level treatment center, an intersection of two beams emitted by the third ray source and the fourth ray source is a high-level treatment center, and multiple treatment nodes with the low-level treatment center as a spherical center and multiple treatment nodes with the high-level treatment center as a spherical center form a fully-spherical treatment space.

An operation method of a fully-spherical radiation therapy system using the preceding fully-spherical radiation therapy system is provided. The fully-spherical radiation therapy system further includes a multi-degree-of-freedom treatment couch, and the method includes steps described below.

An X-ray computed tomography (CT) image or a magnetic resonance imaging (MRI) diagnostic image of a patient is input into a treatment planning system, a target volume of a tumor and critical organs are delineated, treatment nodes are selected from a fully-spherical treatment space, treatment dose distributions are calculated and a dose is allocated to each treatment node, and a treatment plan is developed, where the fully-spherical treatment space includes a low-level treatment center treatment space and a high-level treatment center treatment space.

Treatment path planning is performed for a treatment node of the low-level treatment center treatment space and a treatment node of the high-level treatment center treatment space, a double-image-guided positioning mechanism performs image-guided setup verification on the patient on the multi-degree-of-freedom treatment couch to detect a position deviation of the patient, and the multi-degree-of-freedom treatment couch automatically corrects the position deviation of the patient.

A multi-degree-of-freedom robot carrying a linear accelerator reaches a treatment node on the fully-spherical treatment space; according to a treatment path planned by the treatment plan, the multi-degree-of-freedom robot carrying the linear accelerator completes beam projection of a treatment node of a low-level treatment center, and the multi-degree-of-freedom robot carrying the linear accelerator switches to a high-level treatment center to complete beam projection of a treatment node of the high-level treatment center.

BRIEF DESCRIPTION OF DRAWINGS

FIG. 5 (b) is another schematic diagram showing imaging geometry of a fully-spherical radiation therapy system according to an embodiment of the present application;

FIG. 6 (a) is another schematic diagram of conversion from an actual projection plane of a high-level treatment center image-guided positioning mechanism to a virtual projection plane of the high-level treatment center image-guided positioning mechanism according to an embodiment of the present application;

FIG. 8 (b) is a schematic view of a treatment example using a combined treatment mode of a high-level treatment center and a low-level treatment center under a high-level treatment center state according to an embodiment of the present application;

FIG. 8 (c) is a schematic view of a treatment example using a combined treatment mode of a high-level treatment center and a low-level treatment center under a low-level treatment center state according to an embodiment of the present application;

FIG. 9 (b) is a schematic view of a treatment example using a treatment mode of a low-level treatment center under a low-level treatment center state according to an embodiment of the present application;

FIG. 10 (b) is a schematic view of a treatment example using a treatment mode of a high-level treatment center under a high-level treatment center state according to an embodiment of the present application.

DETAILED DESCRIPTION

Figure 1:
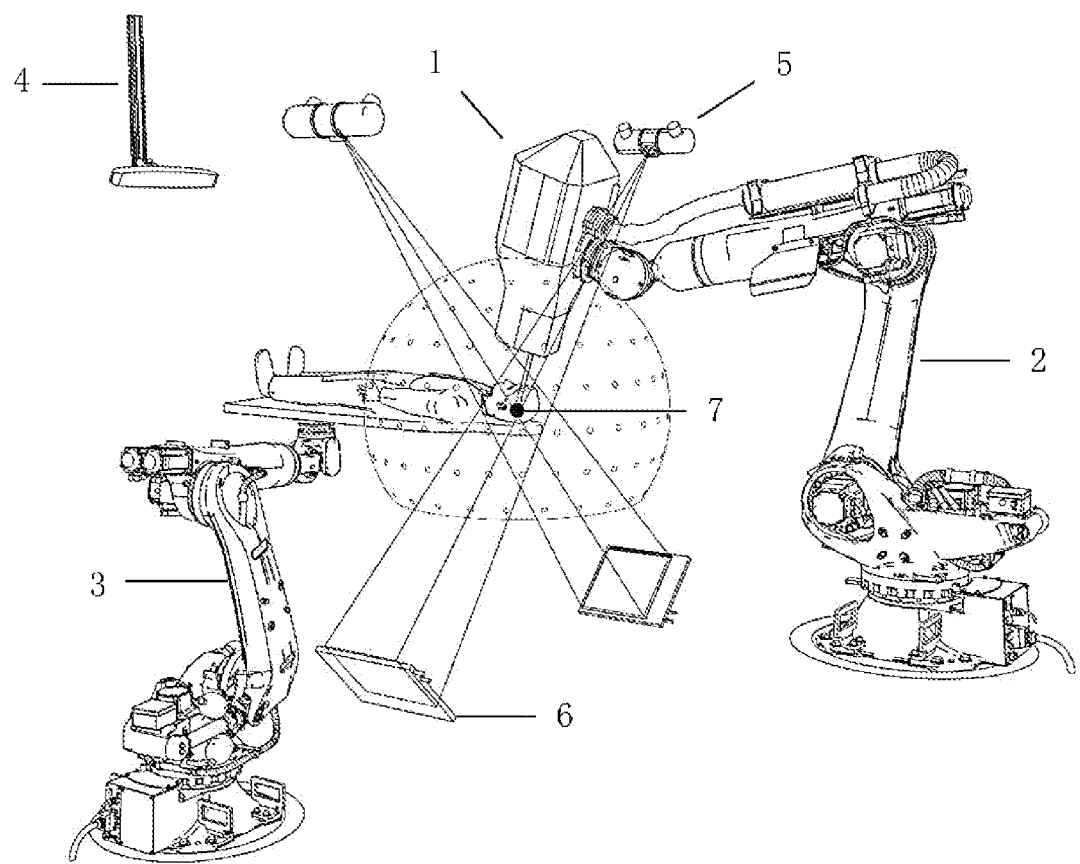
FIG. 1 is a schematic view of a radiosurgery robot system in the related art.
Figure 2:
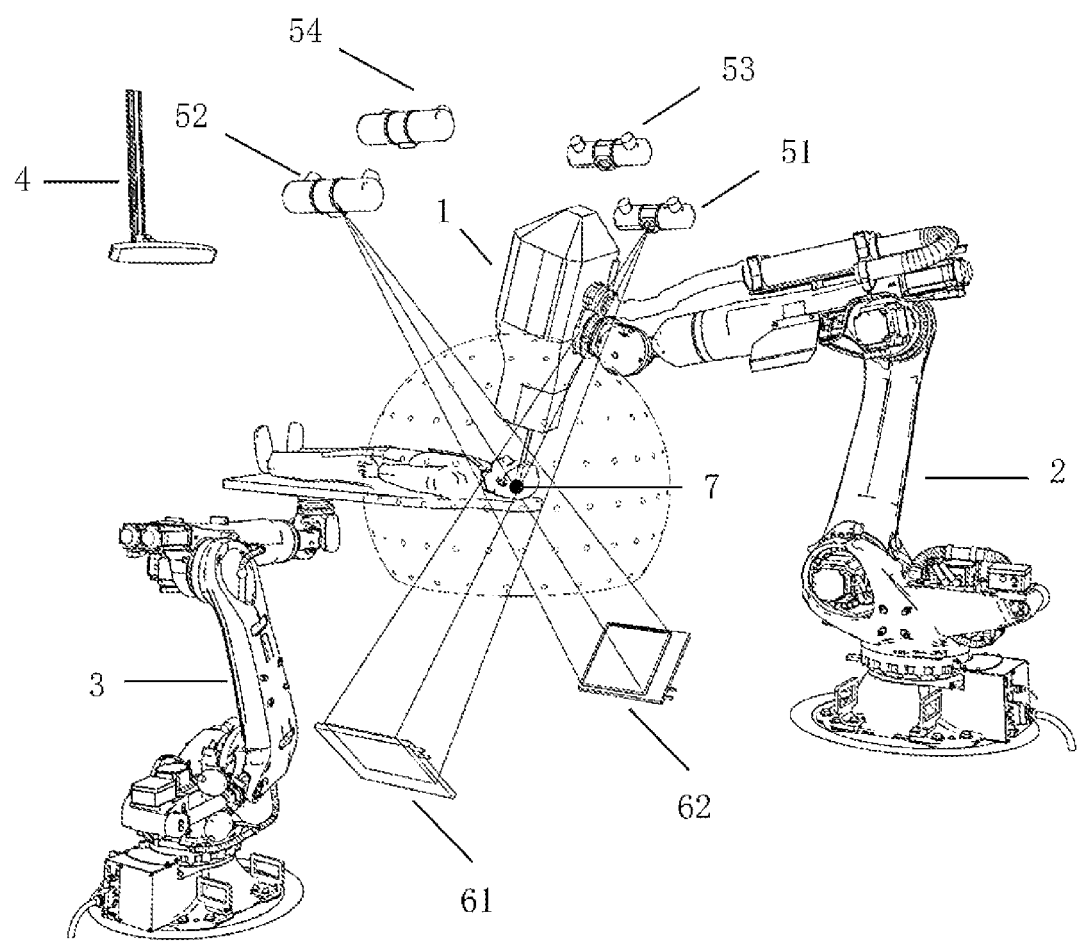
FIG. 2 is a schematic view of treatment using a low-level treatment center treatment space according to an embodiment of the present application.
Figure 3:
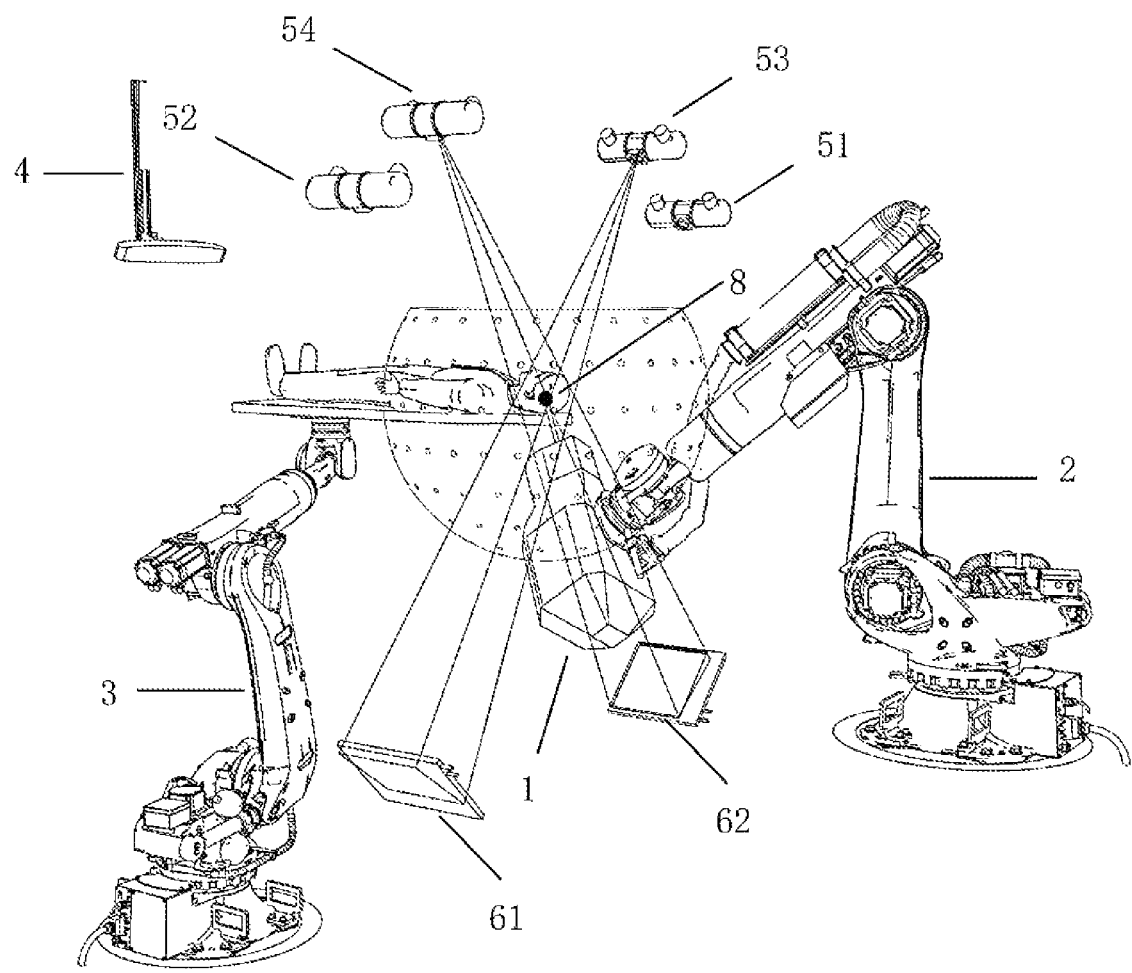
FIG. 3 is a schematic view of treatment using a high-level treatment center treatment space according to an embodiment of the present application.
Figure 4:
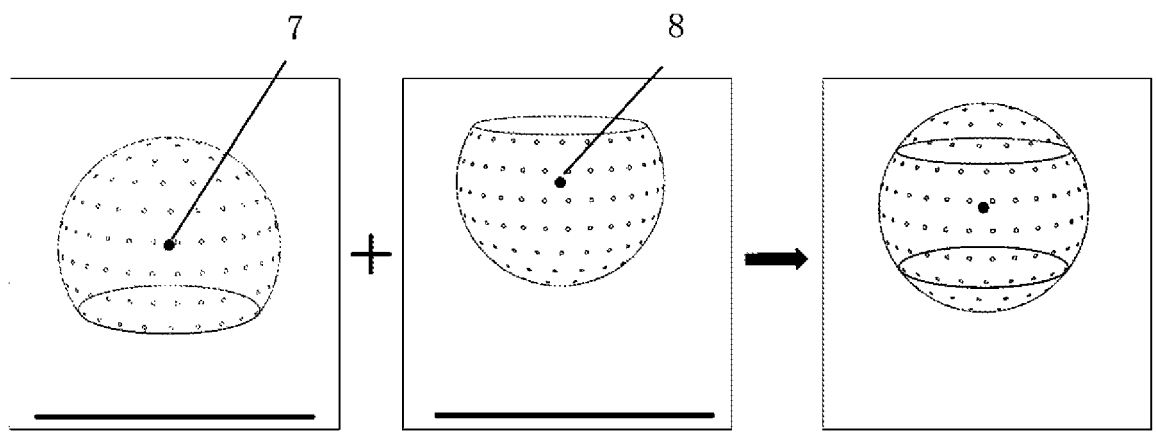
FIG. 4 is a schematic view of a combination of a low-level treatment center treatment space and a high-level treatment center treatment space according to an embodiment of the present application.

A fully-spherical radiation therapy system is provided and the structural composition of the fully-spherical radiation therapy system is shown in FIG. 2 and FIG. 3. The fully-spherical radiation therapy system includes a miniature linear accelerator 1, a six-degree-of-freedom robot 2 carrying the accelerator, a six-degree-of-freedom robotic treatment couch 3, a breathing motion tracking system 4, an image-guided positioning system corresponding to a low-level treatment center 7 and an image-guided positioning system corresponding to a high-level treatment center 8 (a treatment center at a lower position is referred to as the low-level treatment center, and a treatment center at a higher position is referred to as the high-level treatment center). The breathing motion tracking system 4 uses the infrared optical motion tracking technology to detect the body surface motion in real time, and thus achieves the real-time motion tracking of a target volume in vivo in combination with the image-guided positioning system. The imaging hardware of the double-image-guided positioning system is composed of four X-ray tubes, four high voltage generators (generally disposed between devices) corresponding to the four X-ray tubes and two X-ray flat-panel detectors. A low-level treatment center image-guided positioning mechanism takes the low-level treatment center 7 as the imaging center, and the composition of the imaging hardware of the mechanism is shown in FIG. 2. X-ray tube one 51 and flat-panel detector one 61 generate an X-ray image on one projection plane, and X-ray tube two 52 and flat-panel detector two 62 generate an X-ray image on another projection plane. A high-level treatment center image-guided positioning mechanism takes the high-level treatment center 8 as the imaging center, and the composition of the imaging hardware of the mechanism is shown in FIG. 3. X-ray tube three 53 and flat-panel detector one 61 generate an X-ray image on one projection plane, and X-ray tube four 54 and flat-panel detector two 62 generate an X-ray image on another projection plane. As shown in FIG. 4, the low-level treatment center 7 forms a low-level treatment center treatment space above and on two sides of a patient, and the high-level treatment center 8 forms a high-level treatment center treatment space below and on two sides of the patient. The combination of the low-level treatment center treatment space and the high-level treatment center treatment space provides a fully-spherical treatment space.

Figure 5:
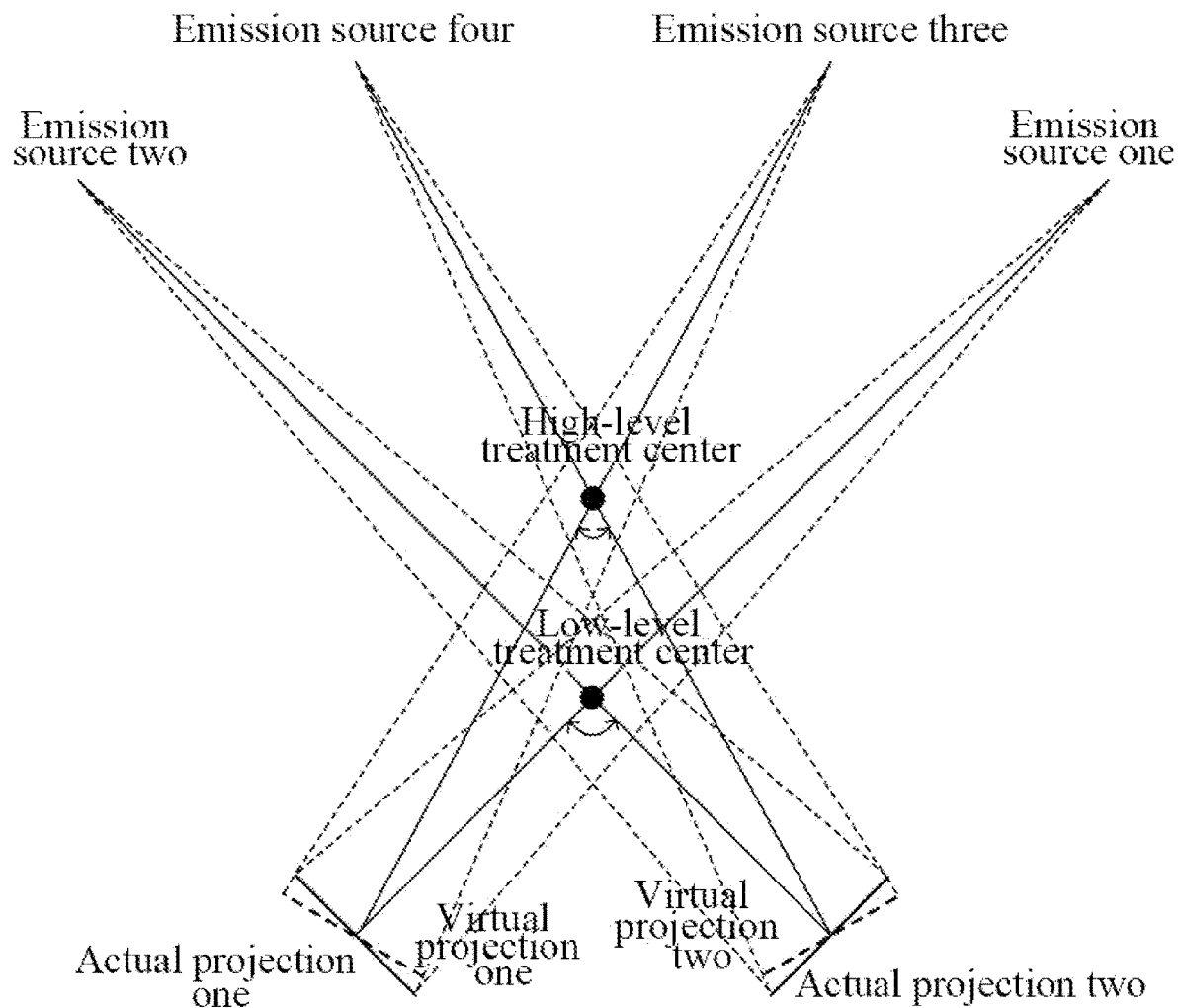
FIG. 5 (a) is a schematic diagram showing imaging geometry of a fully-spherical radiation therapy system according to an embodiment of the present application.
Figure 5:
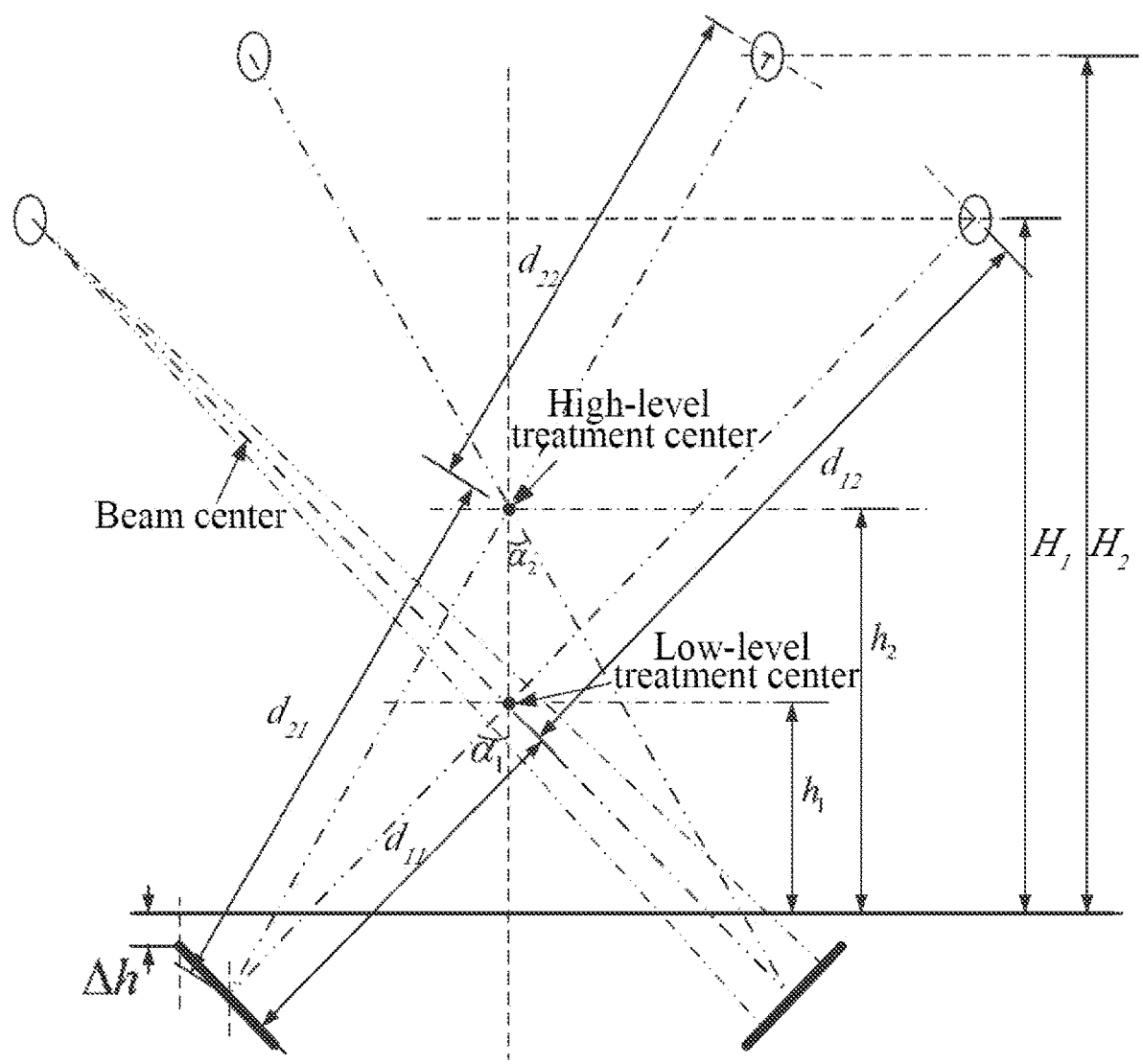

As shown in FIG. 5 (a), the imaging geometry of the image-guided positioning system of the fully-spherical radiation therapy system is as follows: a first ray source and a second ray source emit ray beams, respectively, which cross so that the low-level treatment center 7 is obtained, and actual projection one and actual projection two are generated on the two flat-panel detectors; a third ray source and a fourth ray source emit ray beams, respectively, which cross so that the high-level treatment center 8 is obtained, and two actual projections are generated on the two flat-panel detectors and then are converted into virtual projection one and virtual projection two, respectively.

Mounting positions of multiple components of the radiation therapy system and the adaptation relationships between the multiple components are key parameters and design priorities of the technical solution of the present application. The height of the low-level treatment center, the height of the high-level treatment center and the relative height between the low-level treatment center and the high-level treatment center need to be designed due to the limitation of the ceiling height from the ground and the requirements for ensuring image quality. The distance from a center of a bulb tube source of an X-ray tube to the flat-panel imaging center also greatly affect the imaging quality. At the same time, it is necessary to consider the influence of the source-axis distance (SAD), the treatment couch travel and components such as the radiation source center of the accelerator. Under the conditions of ensuring no collision between hardware, no collision between hardware and the ground and no collision between hardware and the treatment safe zone, the six-degree-of-freedom mechanical arm carrying an accelerator machine head should be capable of reaching as many spatial positions as possible above, below and on two sides of the patient. Therefore, it is necessary to perform overall design and verification in consideration of the preceding mounting conditions.

Based on the preceding considerations, the present application performs theoretical calculation on position relationships between multiple components and performs design according to the results, and performs simulation and practical verification on the design scheme so as to achieve the convenience of various practical operations during the treatment and satisfy the balance requirements for the imaging quality under various conditions. Referring to the structure and multiple parameters shown in FIG. 5 (b), the following definition relationships are adopted:

$$3575 \leq d_{11} + d_{12} \leq 3700 \quad (1);$$

$$0.54 \leq h_1/d_{11} \leq 0.58 \quad (2);$$

$$3515 \leq d_{21} + d_{22} \leq 3600 \quad (3);$$

$$0.68 \leq h_2/d_{21} \leq 0.72 \quad (4); \text{ and}$$

$$0.42 \leq (h_2 - h_1)/h_1 \leq 0.56 \quad (5).$$

$d_{11}$ represents the distance from the low-level treatment center 7 to an imaging center of flat panel-detector one 61; $d_{12}$ represents the distance from the low-level treatment center 7 to a center of a bulb tube source of X-ray tube one 51 of the low-level treatment center point; $d_{21}$ represents the distance from the high-level treatment center 8 to an imaging center of flat-panel detector one 61; $d_{22}$ represents the distance from the high-level treatment center 8 to a center of a bulb tube source of X-ray tube three 53 of the high-level treatment center point; $h_1$ represents the height from the low-level treatment center 7 to the ground; and $h_2$ represents the height from the high-level treatment center 8 to the ground.

In addition, the technical solution of the present application, in addition to needing to simultaneously satisfy the mounting conditions of the preceding formulas (1) to (5), also needs to satisfy the following conditions: the height $H_1$ from X-ray tube one 51 of the low-level treatment center image-guided positioning mechanism to the ground ranges from 2000 mm to 2200 mm; the height $H_2$ from X-ray tube three 53 of the high-level treatment center image-guided positioning mechanism to the ground ranges from 2500 mm to 2700 mm; and the intersection angle between the included angle $\alpha_1$ between the low-level treatment center beam center and the vertical plane and the included angel $\alpha_2$ between the high-level treatment center beam center and the vertical plane ranges from 15° to 60°, and $\alpha_1 > \alpha_2$. For example, in the present application, the position of the flat-panel detector may be adjusted to be located on the ground or below the ground. To ensure the height from the high-level treatment center 8 to the ground and the range of the treatment couch travel, the flat-panel detector is preferably placed 10 mm to 50 mm below the ground.

For example, to simplify multiple alignments of the image-guided positioning system, four ray sources and two flat-panel detectors are provided with fixed positions, that is, the position of the low-level treatment center 7 and the position of the high-level treatment center 8 are fixed. During the treatment, the couch only needs to be raised or lowered to the low-level treatment center 7 or the high-level treatment center 8 according to the treatment requirements.

The low-level treatment center image-guided positioning mechanism and the high-level treatment center image-guided positioning mechanism share flat-panel detectors in two projection directions. The beam emitted by the X-ray ray source of the low-level treatment center image-guided positioning mechanism is perpendicular to the actual projection plane of the flat-panel detector so that an orthographically projected X-ray image is generated for the two-dimensional/three-dimensional image registration method for an X-ray image and a computed tomography (CT) image which are for image-guided positioning. For the preceding process, reference may be made to the two-dimensional/three-dimensional medical image registration method based on two flat panels in the related art.

Figure 6:
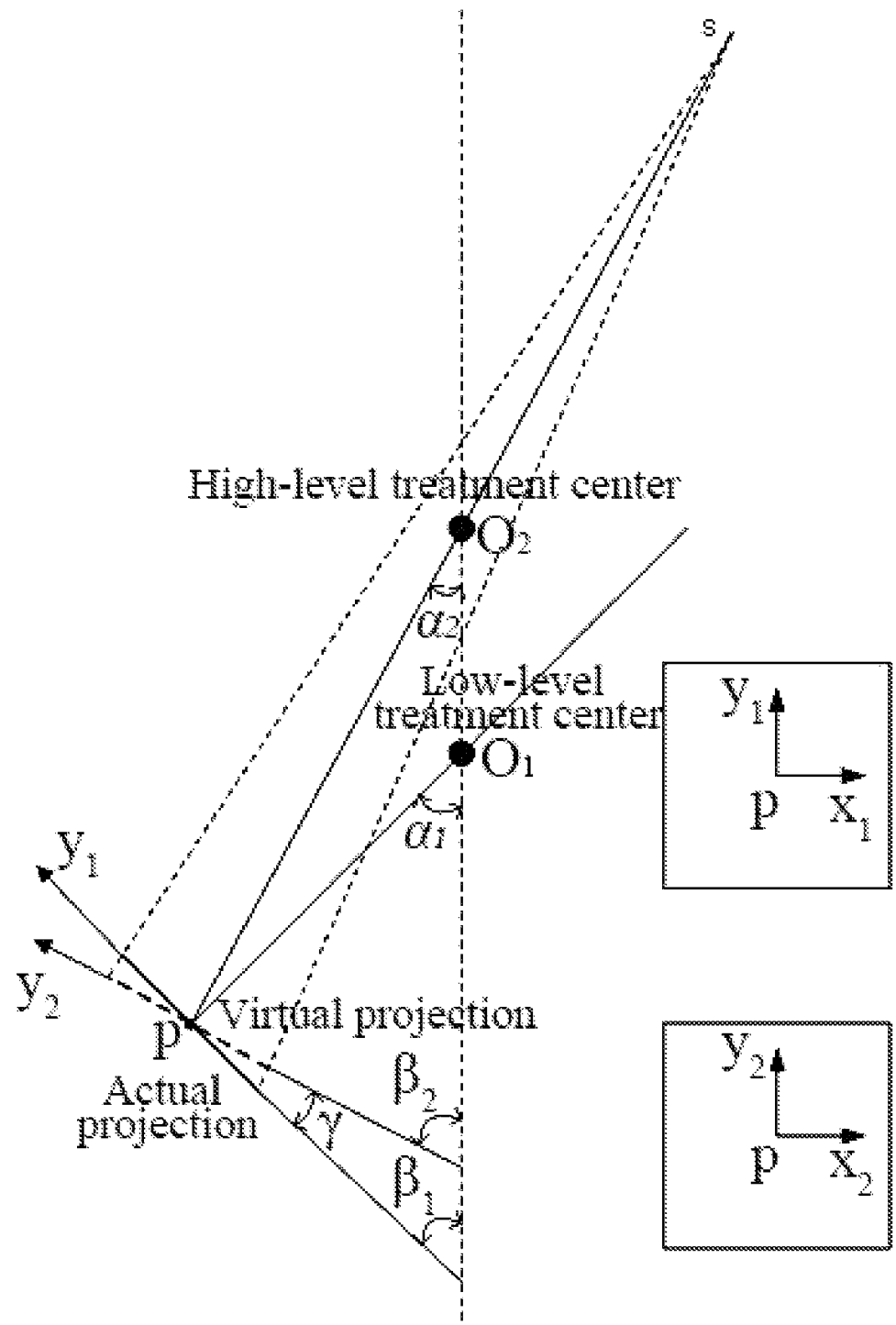
FIG. 6 is a schematic diagram of conversion from an actual projection plane of a high-level treatment center image-guided positioning mechanism to a virtual projection plane of the high-level treatment center image-guided positioning mechanism according to an embodiment of the present application.
Figure 6:
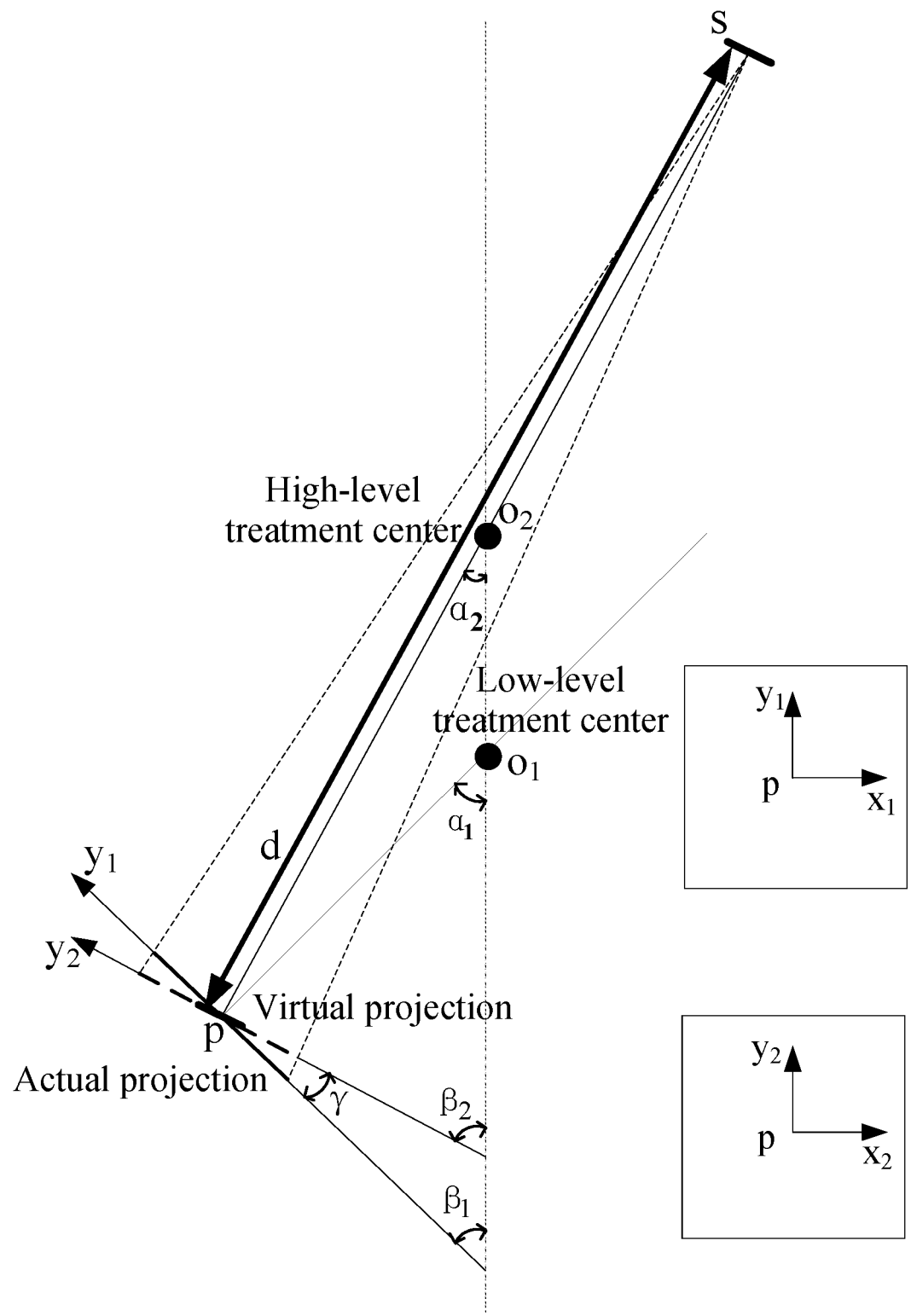

The beam emitted by the ray source of the high-level treatment center image-guided positioning mechanism is not perpendicular to the actual projection plane of the flat-panel detector, so that an obliquely projected X-ray image is generated. To perform image registration on the X-ray image and the three-dimensional CT image so as to calculate the deviation position of the patient, a virtual imaging plane perpendicular to the projection direction is set in the orthographic projection direction, so that the acquired X-ray image is subjected to the conversion from the actual imaging plane to the virtual imaging plane, and thus an orthographically projected X-ray image is generated, which is conducive to using the two-dimensional/three-dimensional image registration method of the preceding patents. A virtual projection plane is set first, and the beam emitted by the X-ray ray source is enabled to be perpendicular to the virtual projection plane; and then the image on the actual oblique projection plane is converted into an orthographically projected image on the virtual projection plane. As shown in FIG. 6 and FIG. 6 (a), $x_1py_1$ and $x_2py_2$ are two-dimensional coordinate systems of the actual projection plane and the virtual projection plane, respectively, the included angle between the two coordinate system planes is $\gamma$, and the distance from the central point of the X-ray ray source to the central point of the flat-panel detector is d.

$$\beta_1 = 90° - \alpha_1$$

$$\beta_2 = 90° - \alpha_2$$

$$\gamma = \beta_2 - \beta_1 = \alpha_1 - \alpha_2$$

It is assumed that $(x_1, y_1)$ represents a coordinate point on the coordinate system of the actual oblique projection plane $x_1py_1$, and then the corresponding coordination point $x_1py_1$ on the coordinate system of the virtual orthographic projection plane $x_2py_2$ satisfies following formulas:

$$y_2 = \frac{d * y_1 \cos\gamma}{d - y_1 \sin\gamma};$$

$$x_2 = \sqrt{\left(\frac{d}{d - y_1 \sin\gamma}\right)^2 (x_1^2 + (y_1 \cos\gamma)^2) - y_2^2}.$$

Figure 7:
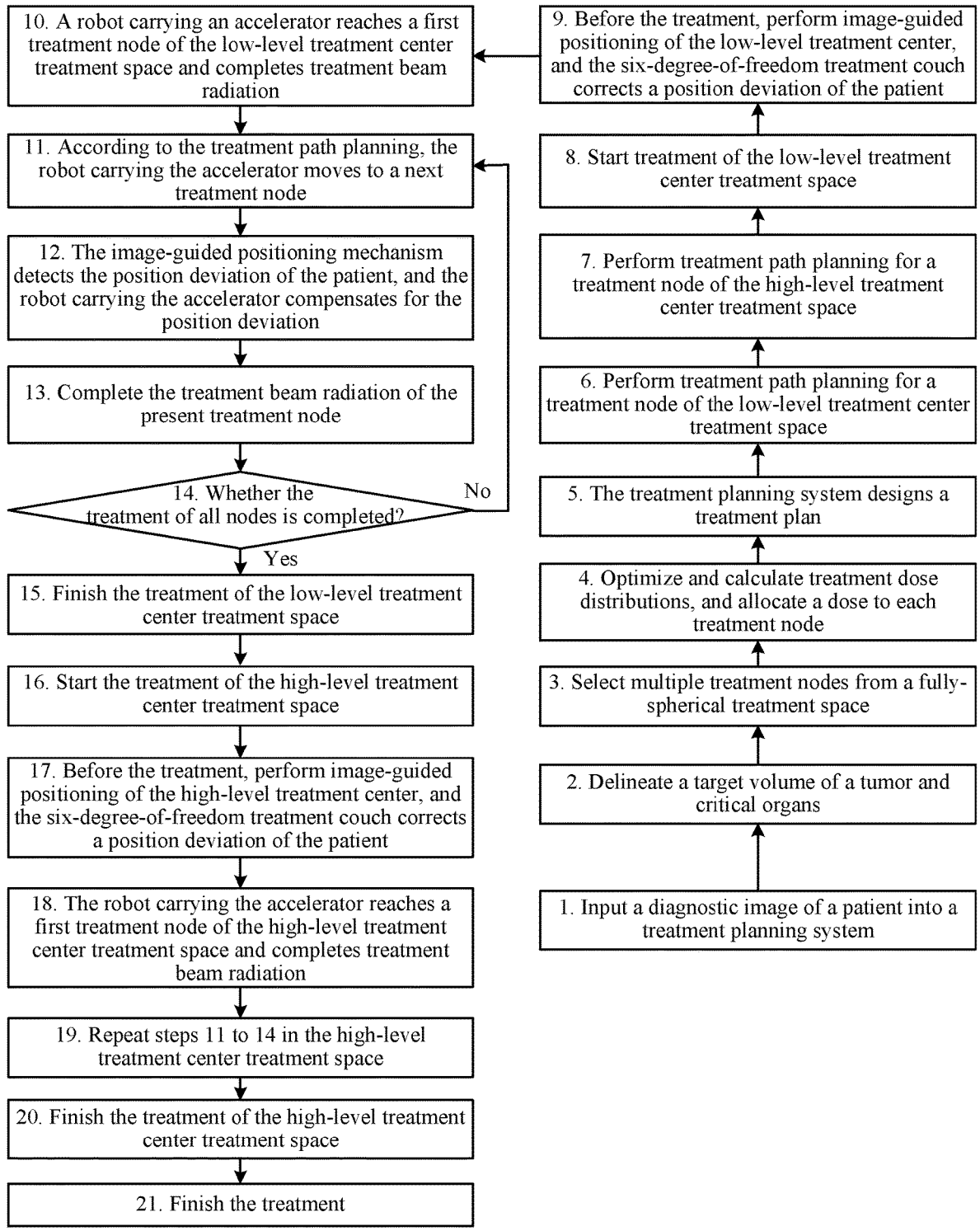
FIG. 7 is a treatment flowchart of a fully-spherical radiation therapy system according to an embodiment of the present application.

The treatment flow of the fully-spherical radiation therapy system is shown in FIG. 7. In a treatment planning stage, a CT image or a magnetic resonance imaging (MRI) diagnostic image of the patient is input into a treatment planning system, a target volume of a tumor and critical organs are delineated, treatment nodes are selected from the fully-spherical treatment space, treatment dose distributions are calculated and a dose is allocated to each treatment node, and a treatment plan is developed. Before the treatment, treatment path planning is performed for a treatment node of the low-level treatment center treatment space and a treatment node of the high-level treatment center treatment space, the image-guided positioning mechanism performs image-guided setup verification on the patient on the treatment couch to detect a position deviation of the patient, and the multi-degree-of-freedom treatment couch automatically corrects the position deviation of the patient. During the treatment, the multi-degree-of-freedom robot carrying the linear accelerator reaches a treatment node on the treatment sphere to perform treatment beam projection, then according to the treatment path planned by the treatment plan, the multi-degree-of-freedom robot carrying the linear accelerator completes beam projection of a treatment node of the low-level treatment center, and the multi-degree-of-freedom robot carrying the linear accelerator switches to the high-level treatment center to complete beam projection of a treatment node of the high-level treatment center.

In the whole treatment process, for static target volumes such as the head and the neck and the spine which do not move due to breathing, the image-guided positioning system continuously detects the position deviation of the patient, and the six-degree-of-freedom robot correspondingly corrects the beam position on each treatment node to compensate for the position deviation of the patient; for target volumes such as the thorax and the abdomen which move due to breathing, the breathing motion tracking system tracks the breathing motion of the target volume in real time, and the six-degree-of-freedom robot drives the accelerator to continuously adjust the treatment beam to compensate for the motion of the target volume, so that motion tracking treatment is achieved.

In an embodiment, a treatment example using a combined treatment mode of a high-level treatment center and a low-level treatment center requires radiation treatment to be performed above and on the back of the patient simultaneously. It is assumed that a total of 5 treatment nodes (the number of treatment nodes in a real case may be several tens or more, and only 5 treatment nodes are illustrated here) exist, treatment node 91, treatment node 92 and treatment node 93 are used for the treatment by the low-level treatment center mode, and treatment node 94 and treatment node 95 are used for the treatment by the high-level treatment center mode. Treatment node 93 is located in both the low-level treatment center treatment space and the high-level treatment center treatment space, and the low-level treatment center mode is used in the embodiment for treatment, as shown in FIG. 8 (a).

Figure 8:
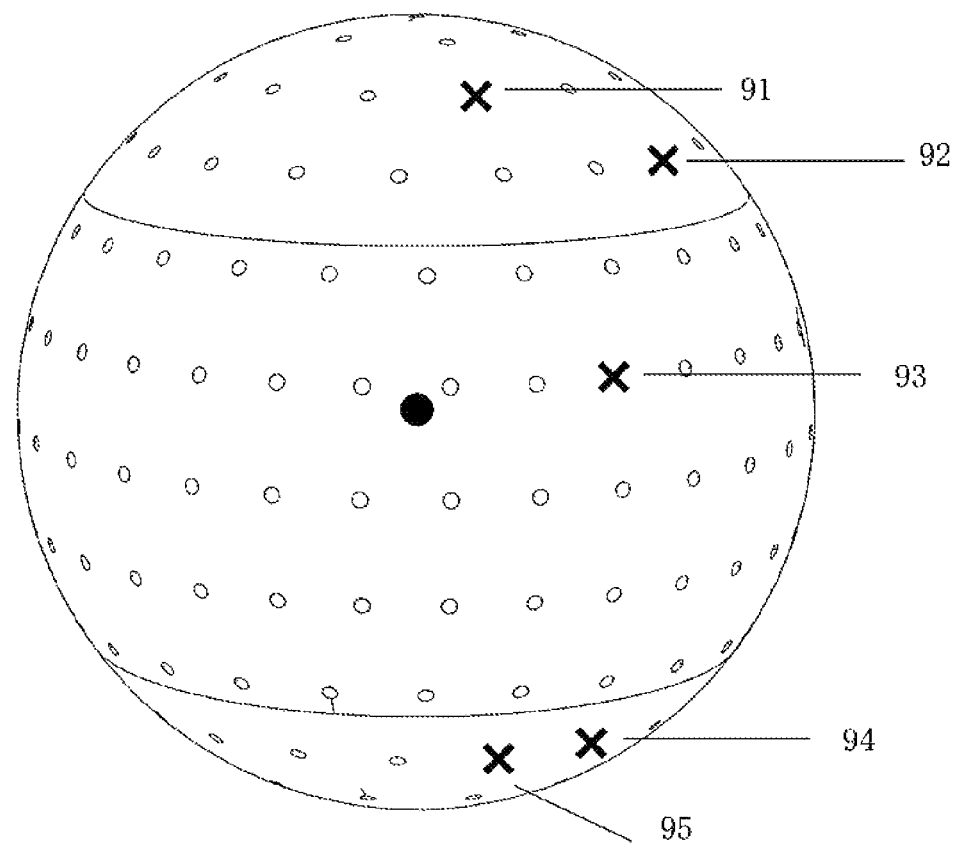
FIG. 8 (a) is a schematic view of selecting treatment nodes in a treatment example using a combined treatment mode of a high-level treatment center and a low-level treatment center according to an embodiment of the present application.
Figure 8:
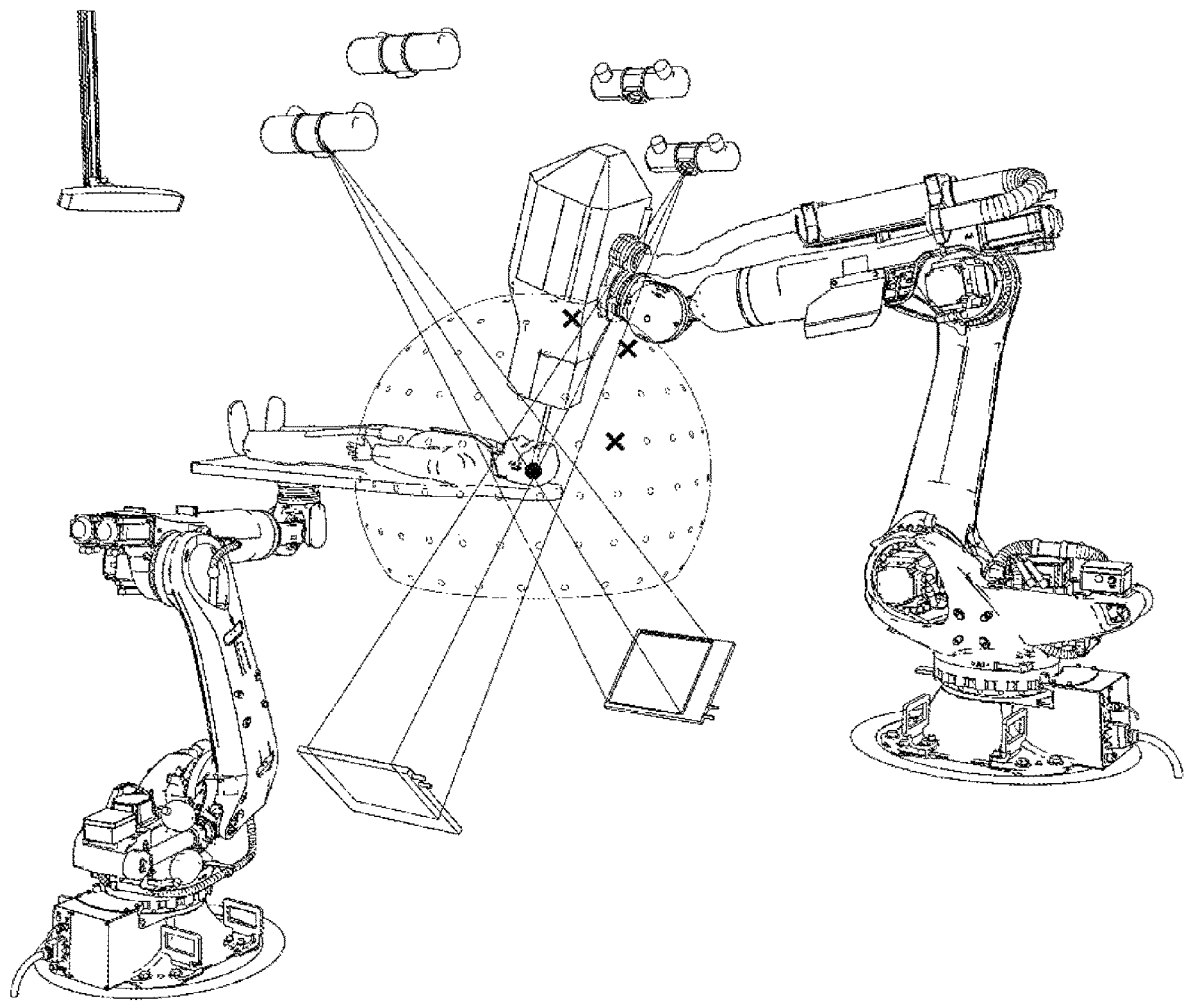
Figure 8:
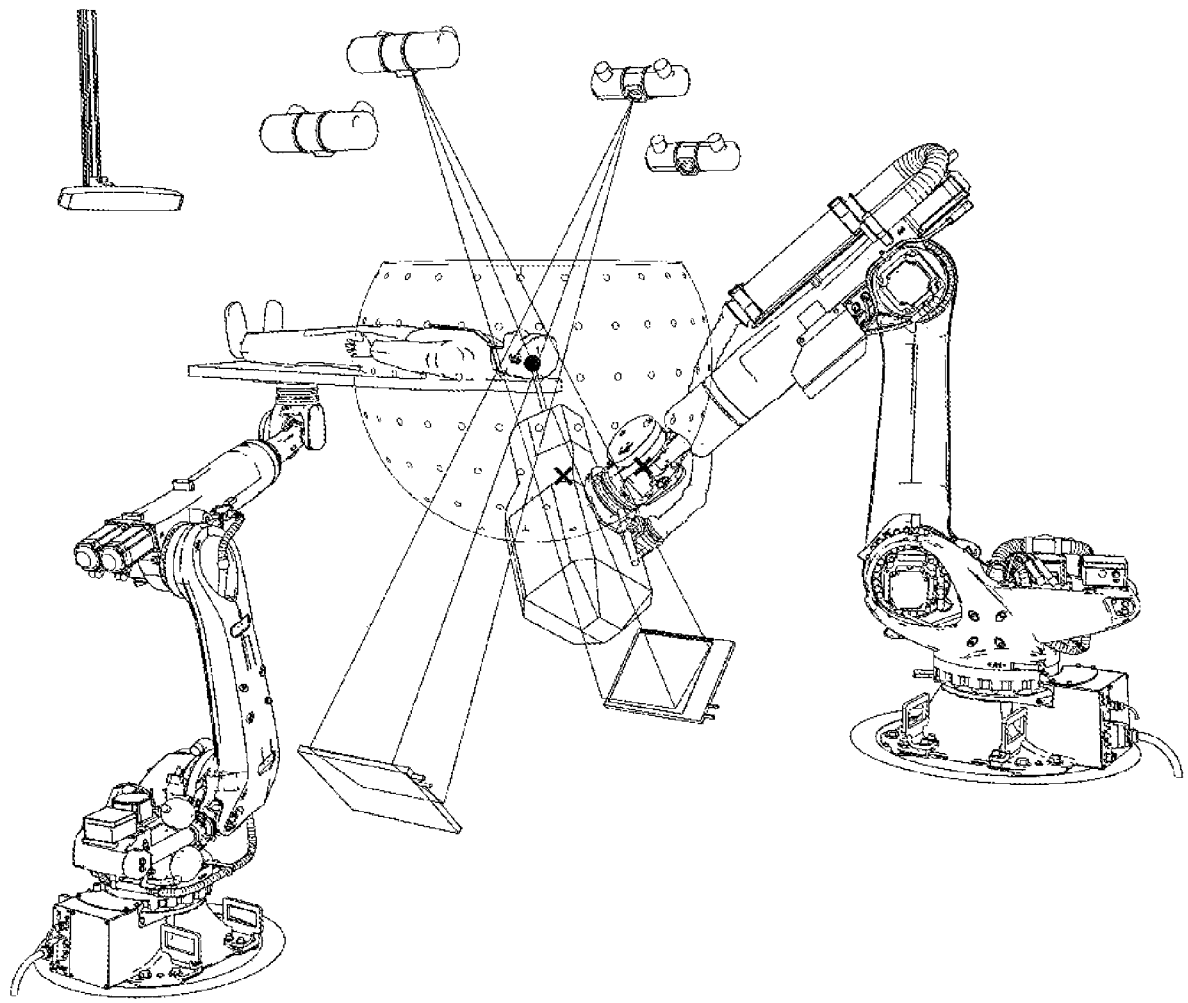

As shown in FIG. 8 (b) to FIG. 8 (c), low-level treatment center image-guided positioning is performed according to the treatment path planned by the treatment plan, where $d_{11}$ is 1650 mm, $d_{12}$ is 2003 mm, $d_{21}$ is 2018 mm, $d_{22}$ is 1553 mm, $h_1$ is 920 mm, $h_2$ is 1400 mm, $\alpha_1$ is 45°, $\alpha_2$ is 35.3°, $H_1$ is 2336.33 mm, and $H_2$ is 2667.14 mm. The six-degree-of-freedom robot carrying the accelerator reaches designated treatment node 91, designated treatment node 92 and designated treatment node 93 on the treatment sphere, sequentially, to perform treatment beam projection and complete the treatment of the low-level treatment center treatment space. Then, the six-degree-of-freedom robot switches to the high-level treatment center image-guided positioning, the six-degree-of-freedom robot carrying the accelerator reaches designated treatment node 94 and designated treatment node 95 on the treatment sphere, sequentially, to perform treatment beam projection and complete the treatment of the high-level treatment center treatment space.

In an embodiment, a treatment example using a treatment mode of a low-level treatment center requires radiation treatment to be performed above and on the side of the patient. It is assumed that a total of 5 treatment nodes (the number of treatment nodes in a real case may be several tens or more, and only 5 treatment nodes are illustrated here) exist, treatment node 101, treatment node 102, treatment node 103, treatment node 104 and treatment node 105 are all used for the treatment by the low-level treatment center mode, as shown in FIG. 9 (a).

Figure 9:
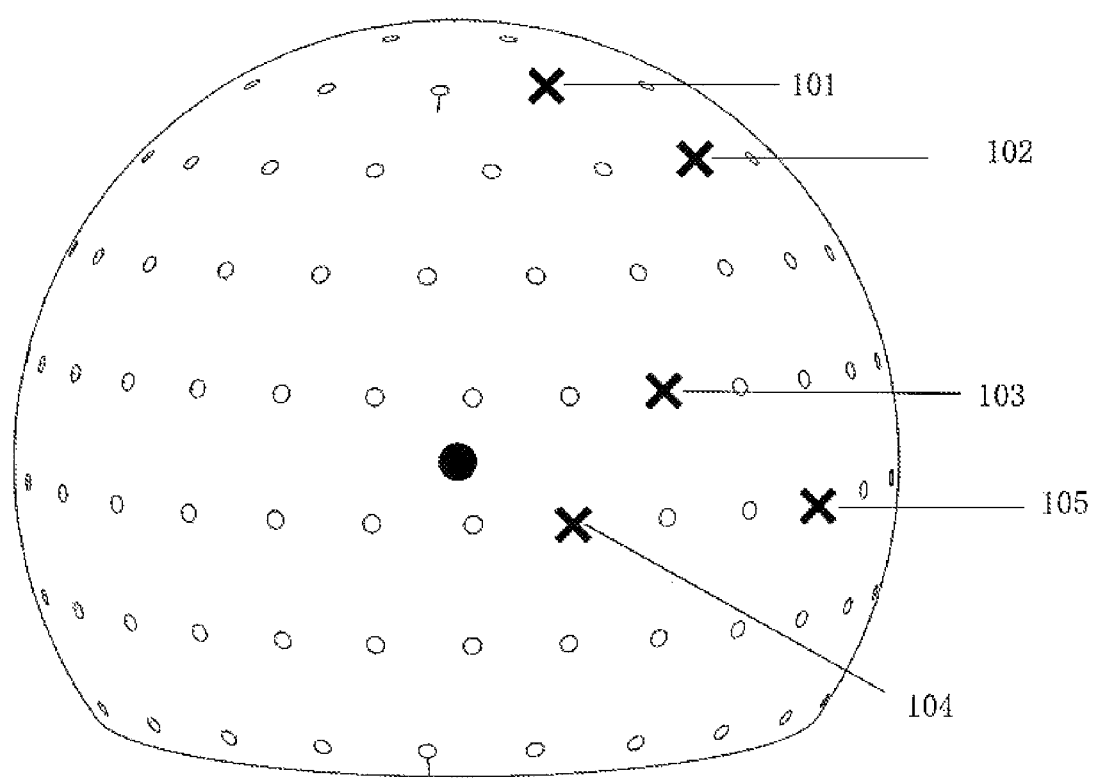
FIG. 9 (a) is a schematic view of selecting treatment nodes in a treatment example using a treatment mode of a low-level treatment center according to an embodiment of the present application.
Figure 9:
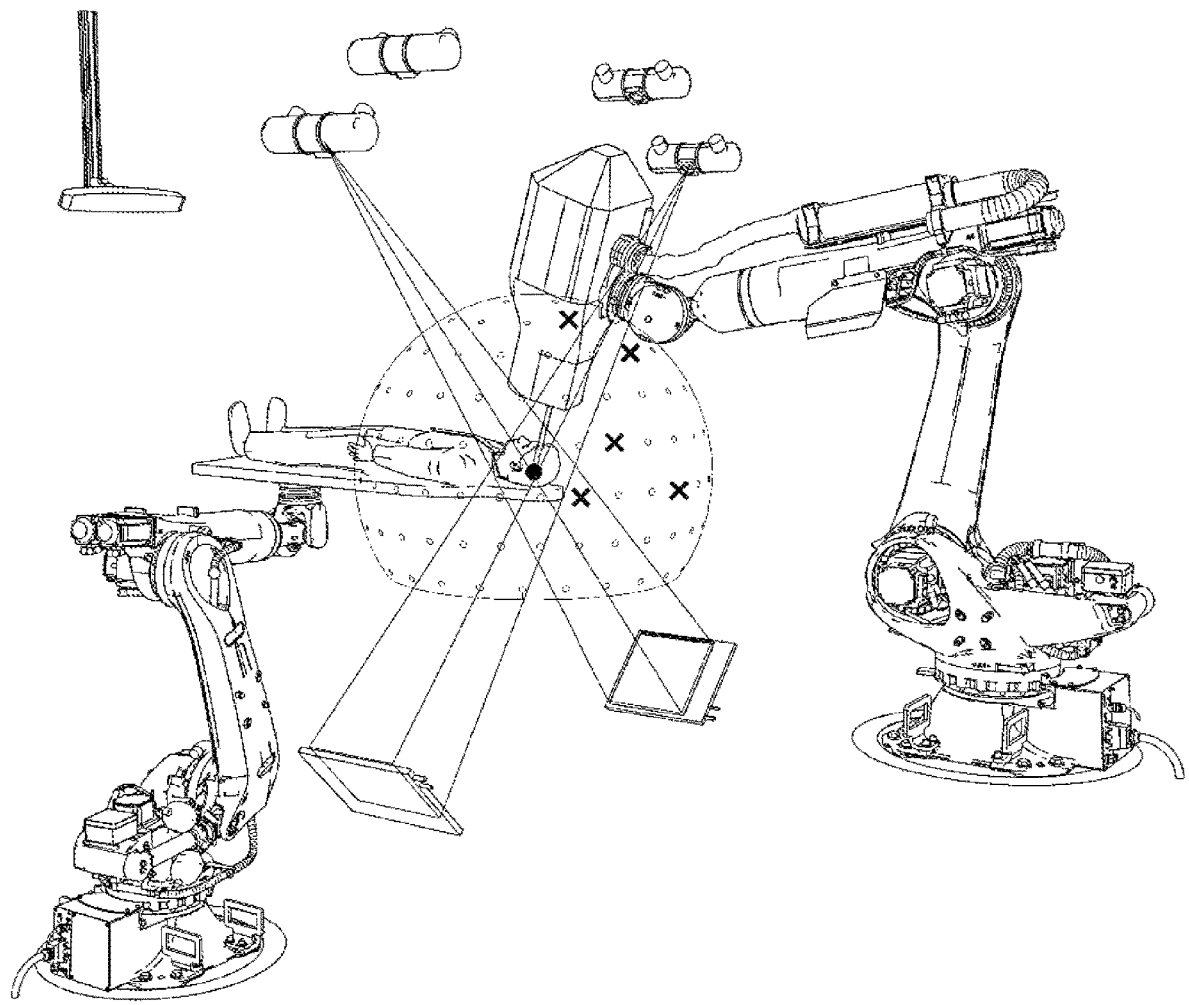

As shown in FIG. 9 (b), low-level treatment center image-guided positioning is performed according to the treatment path planned by the treatment plan, where $d_{11}$ is 1650 mm, $d_{12}$ is 2003 mm, $h_1$ is 920 mm, $\alpha_1$ is 45°, and $H_1$ is 2336.33 mm. The six-degree-of-freedom robot carrying the accelerator reaches designated treatment node 101, designated treatment node 102, designated treatment node 103, designated treatment node 104 and designated treatment node 105 on the treatment sphere, sequentially, to perform treatment beam projection and complete treatment of the low-level treatment center treatment space.

In an embodiment, a treatment example using a treatment mode of a high-level treatment center requires radiation treatment to be performed above and on the side of the patient. It is assumed that a total of 5 treatment nodes (the number of treatment nodes in a real case may be several tens or more, and only 5 treatment nodes are illustrated here) exist, treatment node 111, treatment node 112, treatment node 113, treatment node 114 and treatment node 115 are all used for the treatment by the high-level treatment center mode, as shown in FIG. 10 (a).

Figure 10:
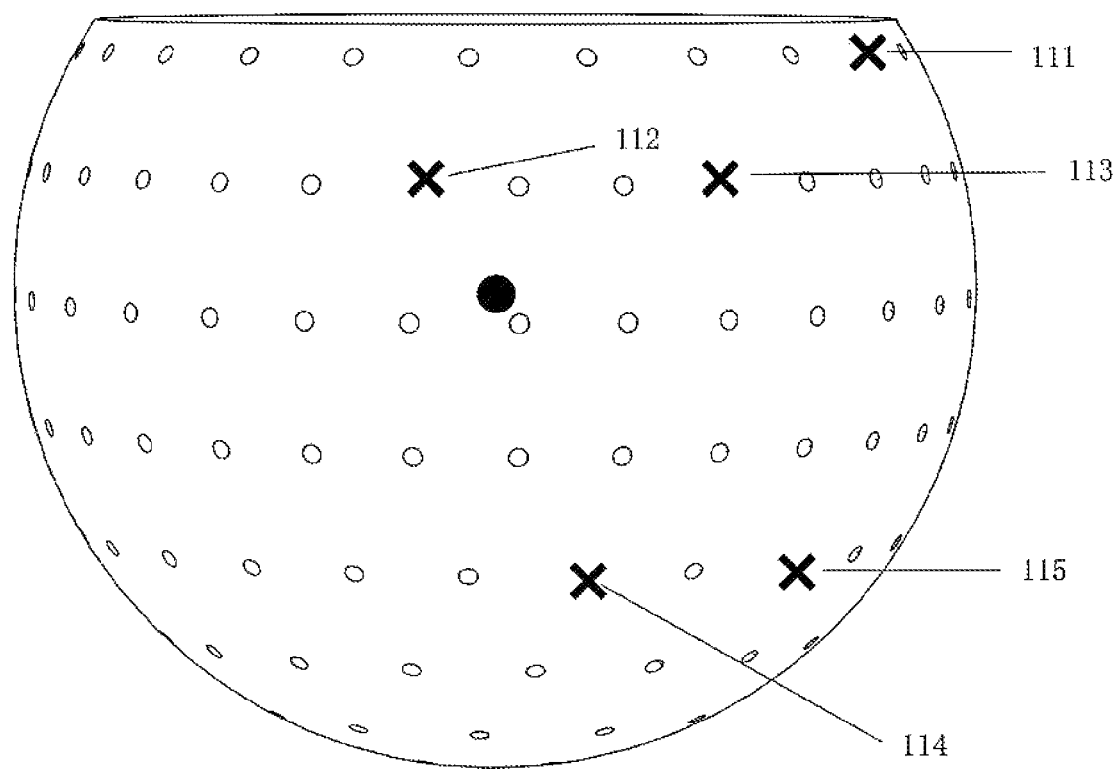
FIG. 10 (a) is a schematic view of selecting treatment nodes in a treatment example using a treatment mode of a high-level treatment center according to an embodiment of the present application.
Figure 10:
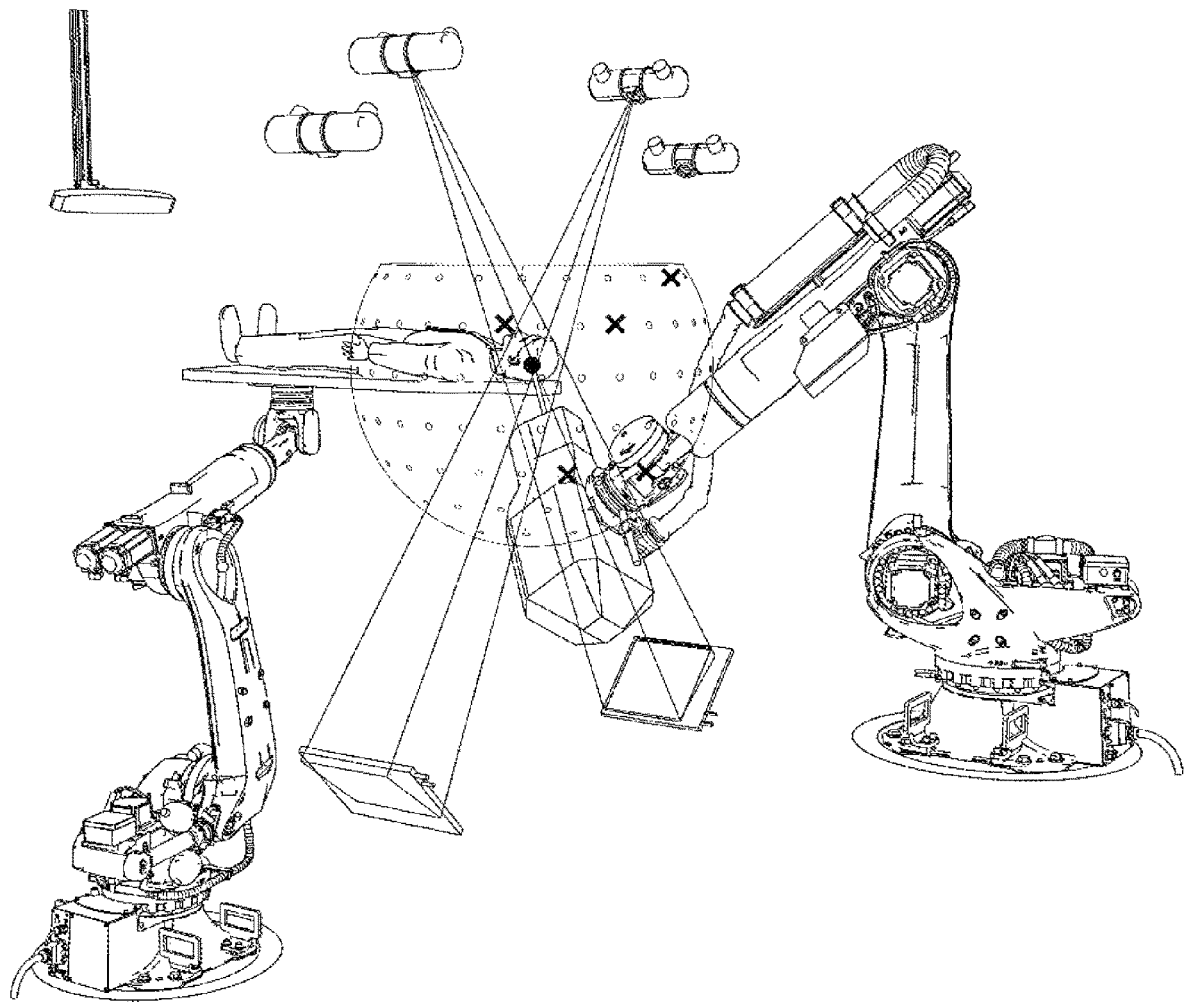

As shown in FIG. 10 (b), high-level treatment center image-guided positioning is performed according to the treatment path planned by the treatment plan, where $d_{21}$ is 2018 mm, $d_{22}$ is 1553 mm, $h_2$ is 1400 mm, $\alpha_2$ is 35.3°, and $H_2$ is 2667.14 mm. The six-degree-of-freedom robot carrying the accelerator reaches designated treatment node 111, designated treatment node 112, designated treatment node 113, designated treatment node 114 and designated treatment node 115 on the treatment sphere, sequentially, to perform treatment beam projection and complete treatment of the high-level treatment center treatment space.

According to the technical solution provided in the present application, the target volume near the back, such as the target volume of the spine and the target volume of the thorax and the abdomen near the back, treatment is performed through the high-level treatment center treatment space, so that the patient can receive effective treatment in a normal supine position. The fully-spherical treatment space combing a low-level treatment center and a high-level treatment center is used, so that more treatment beams can be delivered to multiple target volumes, optimized and more effective treatment dose distributions can be obtained, and therefore a better treatment effect can be achieved. The switch between the low-level treatment center and the high-level treatment center can be achieved quickly only by switching X-ray tubes. Two sets of X-ray tubes share a set of flat-panel detector, so that the treatment system is simplified. Positions of the X-ray tubes and positions the flat-panel detectors are fixed, so that only the treatment couch needs to be adjusted to reach the low-level treatment center or the high-level treatment center during the treatment, and the image-guided positioning system does not need to be recalibrated.

What is claimed is:

1. A fully-spherical radiation therapy system, comprising a multi-degree-of-freedom robot, a linear accelerator and a double-image-guided positioning mechanism, wherein the double-image-guided positioning mechanism comprises four ray sources and two ray detectors, and the four ray sources comprise a first ray source, a second ray source a third ray source and a fourth ray source;

an intersection of two beams emitted by the first ray source and the second ray source is a low-level treatment center, and a first actual projection and a second actual projection are generated on the two ray detectors;

an intersection of two beams emitted by the third ray source and the fourth ray source is a high-level treatment center, two actual projections are generated on the two ray detectors and then are converted into a first virtual projection and a second virtual projection, respectively;

a plurality of treatment nodes with the low-level treatment center as a spherical center and a plurality of treatment nodes with the high-level treatment center as a spherical center form a fully-spherical treatment space;

the multi-degree-of-freedom robot carries the linear accelerator, the multi-degree-of-freedom robot forms a spherical treatment space above and on two sides of a patient around the low-level treatment center and forms a spherical treatment space below and on two sides of the patient around the high-level treatment center;

the two ray detectors are each flat-panel detectors;

a beam emitted by a ray source corresponding to the low-level treatment center image-guided positioning mechanism is perpendicular to an actual projection plane of a corresponding flat-panel detector so that an orthographically projected X-ray image is generated;

a beam emitted by a ray source corresponding to the high-level treatment center image-guided positioning mechanism is not perpendicular to an actual projection plane of a corresponding flat-panel detector so that an obliquely projected X-ray image is generated; and the obliquely projected X-ray image is converted to a virtual imaging plane to obtain an orthographically projected virtual X-ray image, $(x_1, y_1)$ represents a coordinate point on a coordinate system of an oblique projection plane $x_1 p y_1$, and $(x_1, y_1)$ is converted to a corresponding coordinate point $(x_2, y_2)$ on a coordinate system of a virtual orthographic projection plane $x_2 p y_2$ through following formulas:

$$y_2 = \frac{d * y_1 \cos\gamma}{d - y_1 \sin\gamma}, \text{ and}$$

$$x_2 = \sqrt{\left(\frac{d}{d - y_1 \sin\gamma}\right)^2 \left(x_1^2 + (y_1 \cos\gamma)^2\right) - y_2^2};$$

wherein $\gamma$ represents an included angle between a plane of the coordinate system of the oblique projection plane and a plane of the coordinate system of the virtual orthographic projection plane and d represents a distance from a central point of an emission source of an X-ray tube to a central point of a corresponding flat-panel detector.

2. The system according to claim 1, wherein the four ray sources are each X-ray tubes.

3. The system according to claim 2, wherein the low-level treatment center and the high-level treatment center satisfy following conditions:

$3575 \leq d_{11} + d_{12} \leq 3700$, $0.54 \leq h_1/d_{11} \leq 0.58$, $3515 \leq d_{21} + d_{22} \leq 3600$, $0.68 \leq h_2/d_{21} \leq 0.72$, and $0.42 \leq (h_2 - h_1)/h_1 \leq 0.56$;

wherein $d_{11}$ represents a distance from the low-level treatment center to an imaging center of a corresponding flat-panel detector; $d_{12}$ represents a distance from the low-level treatment center to a center of a bulb tube source of a corresponding X-ray tube; $d_{21}$ represents a distance from the high-level treatment center to an imaging center of a corresponding flat-panel detector; $d_{22}$ represents a distance from the high-level treatment center to a center of a bulb tube source of a corresponding X-ray tube; $h_1$ represents a height from the low-level treatment center to a ground; and $h_2$ represents a height from the high-level treatment center to the ground.

4. The system according to claim 2, wherein the double-image-guided positioning mechanism comprises a low-level treatment center image-guided positioning mechanism and a high-level treatment center image-guided positioning mechanism, a height of an X-ray tube of the low-level treatment center image-guided positioning mechanism ranges from 2000 mm to 2200 mm, a height of an X-ray tube of the high-level treatment center image-guided positioning mechanism ranges from 2500 mm to 2700 mm, and an imaging intersection angle of the low-level treatment center image-guided positioning mechanism and the high-level treatment center image-guided positioning mechanism ranges from 30° to 120°.

* * * * *